US 8,044,007 B2

United States Patent
Molenda et al.

(10) Patent No.: US 8,044,007 B2
(45) Date of Patent: Oct. 25, 2011

(54) COMPOSITION FOR KERATIN FIBRES COMPRISING AN ARYLATED SILICONE

(75) Inventors: Michael Molenda, Frankfurt (DE); Martin Hoffmann, Zwingenberg (DE); Mustafa Grit, Gernsheim (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 382 days.

(21) Appl. No.: 12/185,525

(22) Filed: Aug. 4, 2008

(65) Prior Publication Data
US 2009/0041705 A1 Feb. 12, 2009

(30) Foreign Application Priority Data

Aug. 7, 2007 (EP) .................................. 07015477

(51) Int. Cl.
*C11D 1/62* (2006.01)
*C11D 9/36* (2006.01)
(52) U.S. Cl. ........ 510/122; 510/119; 510/123; 510/124; 510/466; 510/490; 510/504
(58) Field of Classification Search .................. 510/119, 510/122, 123, 124, 466, 490, 504
See application file for complete search history.

(56) References Cited

U.S. PATENT DOCUMENTS

| 4,668,666 A * | 5/1987 | Allan et al. ..................... 514/63 |
| 5,955,066 A | 9/1999 | Sako et al. |
| 5,997,851 A * | 12/1999 | Cox et al. ..................... 424/70.1 |
| 7,691,799 B2 * | 4/2010 | Molenda et al. ............... 510/122 |
| 2003/0049292 A1 * | 3/2003 | Turowski-Wanke et al. . 424/401 |
| 2005/0118216 A1 * | 6/2005 | Senee ............................ 424/401 |
| 2005/0232888 A1 * | 10/2005 | Weber et al. ................ 424/70.12 |
| 2006/0107469 A1 * | 5/2006 | Anthony et al. ................... 8/405 |
| 2007/0036739 A1 * | 2/2007 | Feng ............................ 424/70.7 |
| 2007/0065392 A1 * | 3/2007 | Simonnet .................... 424/70.31 |
| 2007/0077221 A1 * | 4/2007 | Seigneurin et al. ........ 424/70.16 |
| 2007/0293577 A1 * | 12/2007 | Kamachi et al. ............... 514/574 |
| 2008/0279901 A1 * | 11/2008 | Prigent et al. ................. 424/401 |
| 2009/0234153 A1 * | 9/2009 | Aoki et al. ..................... 560/196 |
| 2010/0278764 A1 * | 11/2010 | Mougin et al. .................. 424/59 |

FOREIGN PATENT DOCUMENTS

| DE | 19950711 A1 | 5/2001 |
| EP | 1787634 | * 5/2007 |
| EP | 1787634 A | 5/2007 |
| WO | 9408557 A | 4/1994 |
| WO | 9955295 A | 11/1999 |
| WO | 0006107 A | 2/2000 |
| WO | 0015180 A | 3/2000 |

OTHER PUBLICATIONS

English Language Abstract for DE 19950711, filed May 3, 2001.

* cited by examiner

*Primary Examiner* — Charles Boyer
(74) *Attorney, Agent, or Firm* — Norris McLaughlin & Marcus

(57) ABSTRACT

The present invention relates to a conditioning and shine enhancing composition for keratin fibers especially human hair. Accordingly the subject of the present invention is an aqueous composition comprising at least one mono alkyl quaternary ammonium surfactant at a concentration of 0.01 to 10% by weight, and at least one arylated silicone at a concentration of 0.001 to 5% by weight, calculated to total composition.

13 Claims, No Drawings

COMPOSITION FOR KERATIN FIBRES COMPRISING AN ARYLATED SILICONE

The present invention relates to a conditioning and shine enhancing composition for keratin fibres especially human hair.

Hair conditioning compositions have widely been used for improving primarily combability of hair and furthermore enhancing smoothness, elasticity and shine. Many types of conditioners have been found on the market varying from emulsions, which are generally rinsed of from hair after application and certain period of processing time, to low viscosity lotions used without rinsing off after application. Hair shine improvement has been one of the main areas of development. Hair shine is very much related to the surface structure of hair and this varies very much with the degree of damage either by environmental effects or chemical treatment of hair such as permanent shaping or oxidative colouring. Although consumers with healthy non-damaged hair are generally satisfied with hair shine, shine of damaged hair is usually found to be unsatisfactory. There have been studies aiming improving shine of especially damaged hair.

The inventors of the present invention have surprisingly found out that a composition comprising at least one mono alkyl quaternary ammonium surfactant and at least one arylated silicone improves shine excellently and conditions hair in terms of combability, elasticity, smoothness and softness.

Accordingly the subject of the present invention is an aqueous composition comprising at least one mono alkyl quaternary ammonium surfactant at a concentration of 0.01 to 10% by weight, and at least one arylated silicone at a concentration of 0.001 to 5% by weight, calculated to total composition.

Compositions of the present invention comprise at least one quaternary ammonium surfactant at a concentration of 0.01 to 10%, preferably 0.05 to 7.5%, more preferably 0.1 to 5% by weight calculated to total composition.

As a rule any mono alkyl quaternary ammonium surfactants are suitable for the compositions of the present invention. With the term mono alkyl it is meant that quaternary ammonium surfactant includes only 1 alkyl chain which has more than 8 C atoms. The term does not exclude that the quaternary ammonium surfactant includes further short alkyl chains present n the molecule.

Preferably at least one mono alkyl quaternary ammonium surfactant is selected from the compounds with the general formula

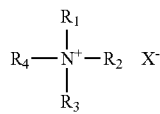

where $R_1$ is saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

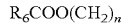

where $R_6$ is saturated or unsaturated, branched or non-branched alkyl chain with 7-21 C atoms and n has typical value of 0-4, and
$R_2$, $R_3$ and $R_4$ are independent from each other lower alkyl chain with 1 to 4 carbon atoms, hydroxyl alky chain with 1 to 4 C atoms, or ethoxy or propoxy group with number of ethoxy or propoxy groups varying in the range of 1 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, stear trimonium chloride, stearamidopropyltrimethylammonium chloride, stearamidopropyl trimonuim chloride.

In addition to the mono alkyl quaternary ammonium surfactant, compositions of the present invention comprise a second quaternary ammonium surfactant which carries two alkyl chains which have more than 8 C atoms. In this respect, in the above formula the group $R_2$ has the meaning as follows:
$R_2$ is saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4.

The rest remains unchanged.

Non-limiting examples to the additional cationic surfactants are distearoyl dimethyl ammonium chloride, dicetyl diethyl ammonium chloride and so called esterquats available on the market, for example, under the trade names "Schercoquat®", "Dehyquart® F30" and "Tetranyl®". Still further examples are so called amidoquatsAgain available on the market, for example, under the trade name "INCROQUAT<sup>â</sup> HO" or "OCS".

Compositions of the present invention comprise at least one arylated silicone. With the term arylated silicone it is meant that any silicone compound comprising at least one aryl group such as phenyl is suitable for the compositions of the present invention.

Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

In the preferred embodiment of the present invention, the arylated silicone comprises at least 2 phenyl groups, more preferably 3, most preferably 4 and in particular 5 phenyl groups in its molecule.

Preferred are diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

More preferred are triphenyl trimethicone, tetramethyl tetraphenyl trisiloxane, tetramethly tetraphenyl trisiloxane and trimethyl pentaphenyl trisiloxane.

Most preferred are tetramethyl tetraphenyl trisiloxane, tetramethly tetraphenyl trisiloxane and trimethyl pentaphenyl trisiloxane.

Particularly preferred arylated silicone is trimethyl pentaphenyl trisiloxane available from Dow Corning under the trade name DC PH-1555 HRI.

It should be noted that compositions of the present invention can also comprise more than one arylated silicone.

Concentration of at least one arylated silicone is in the range of 0.001 to 5%, preferably 0.005 to 3%, more preferably 0.01 to 2.5 and most preferably 0.05 to 2% by weight calculated to total composition. The concentrations referred here are total concentration of arylated silicones in case the compositions comprise more than one silicone.

Compositions of the present invention can be in the form of a thin liquid, emulsion, thickened liquid or gel. Emulsion, thickened liquid and gel compositions are preferred within the meaning of the present invention.

With the term thickened liquid, it is meant that the compositions comprise additionally a thickening agent.

With the term gel it is meant that the compositions comprise additionally a gelling agent and the gelling agent is a polymer forming a shear thinning gel.

The thickening agents include any polymer either natural or synthetic one. Examples are cellulose and its derivatives such as hydroxyethylcellulose, guar and its derivatives such as hydroxypropyl guar. In the selection of the thickening agent, compatibility with cationic surfactant should be carefully examined.

The gelling agents include polymers either synthetic or natural forming shear thinning compositions. Examples to the natural polymers are xanthan gum and its derivatives. Synthetic shear thinning polymers may be those of acrylate polymers such as Carbopol Aqua CC from Noveon, wherein compatibility with cationic surfactant should carefully be examined prior to use.

Concentration of the thickening and/or gelling agents should be in the range of 0.05 to 5%, preferably 0.1 to 2.5% by weight calculated to total content. It should also be noted that gelling and thickening polymers can be used together.

Another preferred form is oil in water (O/W) emulsion. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 20%, preferably 0.5 to 15% and more preferably 1 to 10% by weight calculated to total composition.

Emulsions should also comprise at least one emulsifier. It should be noted that quaternary ammonium compounds with single alkyl chain mentioned above are preferred as emulsifiers as well.

In addition to the cationic surfactants with single alkyl chain, additional emulsifier can be incorporated into the compositions. These additional emulsifiers are surface active substances such as non-ionic, amphoteric or zwitterionic and anionic compounds. Because of the compatibility issues of the anionic surfactants and cationic surfactants mentioned above, anionic surfactants are less suitable and therefore their compatibility should carefully be examined. Otherwise, the compositions of the present invention preferably should substantially be free of anionic surfactants. Preferred emulsifiers are cationic, non-ionic, amphoteric or zwitterionic surfactants. The most preferred additional emulsifiers are non-ionic surfactants.

Suitable non-ionic surfactants are alkyl polyglucosides of the general formula

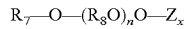

$$R_7-O-(R_8O)_n-O-Z_x$$

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant component as emulsifier, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and—acetate.

Additional emulsifier content of the compositions according to present invention is in the range of 0.05 to 10%, preferably 0.1 to 7.5% and more preferably 0.25 to 5% by weight calculated to total composition.

Compositions of the present invention can comprise additional hair conditioning compounds such as oils, cationic polymers, non-ionic substances. Oils as conditioners according to the present invention are selected from silicone oils either volatile or non-volatile, natural and synthetic oils. Among silicone oils those can be added to the compositions include dimethicone, dimethiconol, polydimethylsiloxane and DC fluid ranges from Dow Corning, cyclosiloxanes such as DC 245. Synthetic oils include mineral oil such as paraffin oil and petrolatum.

Natural oils suitable are such as olive oil, almond oil, avocado oil, weizenkeim oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are as well suitable for the composition of the present invention. Those are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

where $R_9$ and $R_{10}$ are independent from each other saturated, unsaturated or branched or non-branched alkyl chain with 7 to 21 C atoms and n is typically 2-100. Typical concentration range for any of the additional conditioners mentioned above other than cationic conditioning compounds can be in the range of 0.01 to 15% by weight, preferably 0.05-10% by weight, more preferably 0.1-5% by weight calculated to the total composition.

Composition of the present invention comprises cationic polymers as conditioning agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67 and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11010, 30 44 738 and 32 17 059, as well as to the products described in EP-A 337 354 on pages 3 to 7. It is also possible to use mixtures of various cationic polymers.

The cationic polymers also include the quaternized products of graft polymers from organopolysiloxanes and polyethyl oxazolines described in EP-A 524 612 and EP-A 640 643.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", 4$^{th}$ Ed.

The compositions may contain organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvents in the composition should not exceed 15%, preferably between 1 and 10% by weight, calculated to total composition. It should be noted that penetration enhancers are useful for both cleansing and after shampoo conditioning preparations. It is obvious that the concentration in the cleansing compositions is usually lower than in the conditioning preparations.

Compositions of the present invention can comprise UV filters either for stabilization of the product colour or for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxybenzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition.

The compositions of the present invention can comprise hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are those with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably in the range of 0.01 to 0.5% by weight calculated to the total weight of the composition. It should be noted without limiting the use of those ingredients the effect of those hair restructuring ingredients is especially elevated when used in combination with penetration enhancers.

The pH of the compositions according to the invention is in the range of 2 to 7, preferably 3 to 6, more preferably 3 to 5. For adjusting the pH of the said compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be chosen in a way that composition reaches the desired pH value as given above. Typically concentration for acids can be 0.01-3% by weight, preferably 0.05-2% by weight, more preferably 0.05-1.5% by weight calculated to the total composition. The pH of the composition can also be adjusted to the required pH by using alkaline solution such as sodium hydroxide, ammonium hydroxide, potassium hydroxide or their salts with those acids mentioned above in the case that at the selected acid concentration pH of the composition is lower than that of the aimed value.

Compositions of the present invention preferably further comprise synthetic mica as a further shine enhancing component.

Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference. Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

Further in preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Furthermore compositions of the present invention can comprise all substances customarily found in such preparations. Examples of such substances are complexing agents, dyestuffs preferably non-substantive for colouring composition, preservatives, fragrances, etc.

Following examples are to illustrate the invention but not to limit.

EXAMPLE 1

| | % by weight |
|---|---|
| Cetrimonium chloride | 2.0 |
| Trimethyl pentaphenyl trisiloxane | 0.2 |
| Hydroxyethylcellulose | 1.0 |
| Citric acid/Sodium hydroxide | q.s. to pH 4.0 |
| Fragrance | 0.2 |
| Solubilizer* | 0.5 |
| Water | to 100 |

*any solubilizer may be used preferred are those ethoxylated ricinus oil, preferably hydrogenated ricinus oil. In the above example and other examples below where necessary PEG-60 hydrogenated ricinus oil is used preferably at a weight ratio of fragrance to solubilizer 1:1.

The above composition was prepared by combining cetrimonium chloride (a commercially available 25% by weight solution was used) with remaining water and hydroxyethylcellulose. Afterwards fragrance and solubilizer was combined, solubilizer was heated slightly to melt before, and added to the solution of cetrimonium chloride. Finally pentaphenyl trisiloxane was dispersed and pH was adjusted to 4.0.

The above composition was tested in a half side test with 10 consumers having shoulder length hair. Before application of the above composition, hair was washed with a commercially available shampoo. Afterwards to the half side 5 g of the above composition was applied and the other half was left untreated. After processing time of 5 min at ambient temperature the composition was rinsed off from hair. The hair was towel dried and dried with a hair drier. The hair was combable and had excellent shine.

EXAMPLE 2

| | % by weight |
|---|---|
| Cetearyl alcohol | 10.0 |
| Behentrimonium chloride | 2.0 |
| Trimethyl pentaphenyl trisiloxane | 0.5 |
| Citric acid/Sodium hydroxide | q.s. to pH 4.0 |
| Fragrance | 0.4 |
| Water | to 100 |

Above composition was prepared first by emulsifying cetearyl alcohol, behentrimonium chloride and pentaphenyl trisiloxane at a temperature of approximately 75° C. in part of water. Afterwards the composition was cooled down and remaining water was added which was followed by addition of fragrance. Finally pH was adjusted.

For comparative purposes the same composition without arylated silicone was also produced.

The above composition was tested in a half side test against the comparative composition in the same way as in Example 1 with 10 consumers having shoulder length hair. Comments from the consumer were both side feels soft and combable but the side treated with the inventive composition has significantly more shine than the side treated with the comparative composition. The preference was 8/2.

EXAMPLE 3

| | % by weight |
|---|---|
| Cetearyl alcohol | 10 |
| Behentrimonium chloride | 2.0 |
| Dioleylethyl dimonium chloride | 1.0 |
| Trimethyl pentaphenyl trisiloxane | 0.2 |
| Phenyl trimethicone | 0.2 |
| Citric acid/Sodium hydroxide | q.s. to pH 4.0 |
| Fragrance | 0.4 |
| Water | to 100 |

The composition was prepared in the similar way as in Example 2.

In a half side test similar results were obtained as in the Example 2.

Similar results were observed with the compositions below.

EXAMPLE 4

| | % by weight |
|---|---|
| Cetearyl alcohol | 10 |
| Stearylamidopropyl trimonium chloride | 2.0 |
| Trimethyl pentaphenyl trisiloxane | 1.0 |
| Citric acid/Sodium hydroxide | q.s. to pH 4.0 |
| Fragrance | 0.4 |
| Water | to 100 |

EXAMPLE 5

| | % by weight |
|---|---|
| Stearylamidopropyl trimonium chloride | 2.0 |
| Trimethyl pentaphenyl trisiloxane | 0.2 |
| Hydroxyethylcellulose | 1.0 |
| Basic red 51 | 0.1 |
| Citric acid/Sodium hydroxide | q.s. to pH 4.0 |
| Fragrance | 0.4 |
| Solubilizer as in Example 1 | 0.5 |
| Water | to 100 |

EXAMPLE 6

| | % by weight |
|---|---|
| Behentrimonium chloride | 1.5 |
| Synthetic fluorphologopite* | 1.0 |
| Trimethyl pentaphenyl trisiloxane | 1.0 |
| Polyquaternium-37 | 1.5 |
| Benzophenone-3 | 0.2 |
| Citric acid/Sodium hydroxide | q.s. to pH 3.5 |

-continued

| | % by weight |
|---|---|
| Fragrance | 0.4 |
| Solubilizer as in Example 1 | 0.5 |
| Water | to 100 |

*Synthetic fluorphologopite used is commercially available from Sun Chemical Corporation under the trade name SunShine Glitter White with a particle size distribution in the range of 20 to 95 μm.

EXAMPLE 7

| | % by weight |
|---|---|
| Behentrimonium chloride | 1.5 |
| Trimethyl pentaphenyl trisiloxane | 0.6 |
| Dimethicone | 0.6 |
| Polyquaternium 37 | 0.5 |
| BEnzophenone-4 | 0.2 |
| Citric acid/Sodium hydroxide | q.s. to pH 4.5 |
| Fragrance | 0.4 |
| Solubilizer as in Example 1 | 0.4 |
| Water | to 100 |

EXAMPLE 8

| | % by weight |
|---|---|
| Cetrimonium chloride | 1.5 |
| Trimethyl pentaphenyl trisiloxane | 0.2 |
| Dimethicone | 0.5 |
| Hydroxypropyl guar | 0.8 |
| Citric acid/Sodium hydroxide | q.s. to pH 4.5 |
| Fragrance | 0.4 |
| Solubilizer as in Example 1 | 0.4 |
| Water | to 100 |

The invention claimed is:

1. An aqueous composition for conditioning keratin fibres especially for human hair comprising between about 0.01 to 10% by weight of a quaternary ammonium surfactant selected from a compound of the general formula

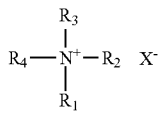

where $R_5CONH(CH_2)_n$, where $R_5$ is saturated or unsaturated branched or non-branched alkyl chain with 7-21 C atoms and n has a value of 0-4, and $R_2$, $R_3$ and $R_4$ are independent from each other and represent a lower alkyl chain with 1 to 4 carbon atoms, hydroxyl alky chain with 1 to 4 C atoms, and ethoxy or propoxy group with number of ethoxy or propoxy groups varying in the range of 1 to 4, and X is chloride, bromide or methosulfate, and between about 0.01 to 5% by weight of an arylated silicone selected from the group consisting of diphenyl dimethicone, diphenylsiloxy phenyl trimethicone, tetramethyl tetraphenyl trisiloxane, triphenyl, trimethicone, and trimethyl pentaphenyl trisiloxane.

2. The aqueous composition according to claim 1 wherein at least one arylated silicone is tetramethyl tetraphenyl trisiloxane.

3. The aqueous composition according to claim 1 wherein at least one arylated silicone is triphenyl trimethicone.

4. The aqueous composition according to claim 1 wherein at least one arylated silicone is trimethyl pentaphenyl trisiloxane.

5. The aqueous composition according to claim 1 further comprising at least one gelling agent.

6. The aqueous composition according to claim 1 further comprising at least one fatty alcohol.

7. The aqueous composition according to claim 1 further comprising at least one organic solvent.

8. The aqueous composition according to claim 1 further comprising at least one UV filter.

9. The aqueous composition according to claim 1 further comprising at least one additional conditioning agent selected from the group consisting of oils, cationic polymers and non-ionic compounds.

10. The aqueous composition according to claim 1 further comprising an additional cationic surfactant.

11. The aqueous composition according claim 10 wherein the additional cationic surfactant selected from compounds according to general formula

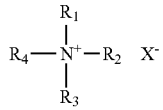

where $R_1$s a saturated or unsaturated, branched or non-branched alkyl chain with 8-22 C atoms or

where $R_5$ is saturated or unsaturated, branched or non-branched alkyl chain with 7-21 C atoms and n has a value of 0-4 or

where $R_6$ is saturated or unsaturated, branched or non-branched alkyl chain with 7-21 C atoms and n has a value of 0-4, and $R_2$ is saturated or unsaturated, branched or non-branched alkyl chain with 8-22 C atoms or

where $R_5$ is saturated or unsaturated, branched or non-branched alkyl chain with 7-21 C atoms and n has a value of 0-4 or

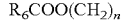

where $R_6$ is saturated or unsaturated, branched or non-branched alkyl chain with 7-21 C atoms and n has a value of 0-4, $R_3$ and $R_4$ are independent from each other lower alkyl chain with 1 to 4 carbon atoms, hydroxyl alky chain with 1 to 4 C atoms, and ethoxy or propoxy group with number of ethoxy or propoxy groups varying in the range of 1 to 4, and X is chloride, bromide or methosulfate.

12. The aqueous composition according to further comprising at least one direct dye.

13. The aqueous composition according to claim 1 further comprising at least one thickening agent.

* * * * *